(12) United States Patent
Bauer

(10) Patent No.: US 11,717,324 B2
(45) Date of Patent: Aug. 8, 2023

(54) PUNCTURE DEVICE FOR CREATING A TIPS SHUNT AND CORRESPONDING METHODS

(71) Applicant: Angiomed GmbH & Co. Medizintechnik KG, Karlsruhe (DE)

(72) Inventor: Martin Bauer, Karlsruhe (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 0 days.

(21) Appl. No.: 17/434,407

(22) PCT Filed: Sep. 2, 2020

(86) PCT No.: PCT/EP2020/074432
§ 371 (c)(1),
(2) Date: Aug. 26, 2021

(87) PCT Pub. No.: WO2022/048738
PCT Pub. Date: Mar. 10, 2022

(65) Prior Publication Data
US 2022/0265317 A1 Aug. 25, 2022

(51) Int. Cl.
*A61B 17/34* (2006.01)
*A61B 17/11* (2006.01)

(52) U.S. Cl.
CPC .......... *A61B 17/3496* (2013.01); *A61B 17/11* (2013.01); *A61B 17/3478* (2013.01);
(Continued)

(58) Field of Classification Search
CPC ............ A61B 17/3496; A61B 17/3478; A61B 2017/347
See application file for complete search history.

(56) References Cited

U.S. PATENT DOCUMENTS

| 4,535,773 A | 8/1985 | Yoon |
| 5,645,076 A * | 7/1997 | Yoon .................. A61B 17/3417 604/165.01 |

(Continued)

FOREIGN PATENT DOCUMENTS

| CN | 101355981 A | 1/2009 |
| CN | 105377324 A | 3/2016 |

(Continued)

OTHER PUBLICATIONS

PCT/EP2020/074432 filed Sep. 2, 2020 International Search Report and Written Opinion dated May 17, 2021.

*Primary Examiner* — Ashley L Fishback
(74) *Attorney, Agent, or Firm* — Rutan & Tucker LLP

(57) ABSTRACT

The present invention relates to a puncture device for creating a TIPS shunt, comprising a puncture needle, a sheath, the sheath being arranged to surround the puncture needle, the puncture needle being slidably arranged inside the sheath so that the puncture needle can be moved between a first position in which the puncture needle protrudes beyond the distal end of the sheath and a second position where a tip of the puncture needle is retracted into the sheath, the sheath and the puncture needle being arranged so that in the second position, blood can be aspirated into the sheath through a gap between the puncture needle and the sheath, a locking means, the locking means being arranged for releasably locking the puncture needle in the first and/or the second position.

12 Claims, 4 Drawing Sheets

(52) U.S. Cl.
CPC . *A61B 2017/1139* (2013.01); *A61B 2017/347* (2013.01); *A61B 2217/005* (2013.01)

(56) References Cited

U.S. PATENT DOCUMENTS

| | | | |
|---|---|---|---|
| 8,657,790 B2 * | 2/2014 | Tal | A61M 25/0618 604/164.08 |
| 9,884,169 B2 * | 2/2018 | Bierman | A61M 25/0668 |
| 2008/0140006 A1 | 6/2008 | Eskur et al. | |
| 2011/0276014 A1 * | 11/2011 | Saitoh | A61B 17/3401 604/272 |
| 2012/0108926 A1 | 5/2012 | Kassab | |
| 2013/0245533 A1 | 9/2013 | Kahn et al. | |
| 2013/0304036 A1 * | 11/2013 | Kimmel | A61B 17/3478 604/528 |
| 2013/0345634 A1 | 12/2013 | Wach et al. | |
| 2014/0142542 A1 | 5/2014 | Rosenbaum et al. | |
| 2014/0171826 A1 | 6/2014 | Lampropoulos et al. | |
| 2015/0297213 A1 * | 10/2015 | Lehtinen | A61B 17/0401 606/232 |
| 2017/0105761 A1 | 4/2017 | Sapir et al. | |
| 2020/0170662 A1 * | 6/2020 | Vardi | A61B 17/32053 |
| 2020/0254214 A1 | 8/2020 | Murphy | |

FOREIGN PATENT DOCUMENTS

| | | |
|---|---|---|
| CN | 106510808 A | 3/2017 |
| CN | 109044504 A | 12/2018 |
| CN | 209004071 U | 6/2019 |
| CN | 210990616 U | 7/2020 |
| DE | 1809364 A1 | 10/1969 |
| EP | 0150281 A1 | 8/1985 |

\* cited by examiner a)
b)

Fig. 3
a)
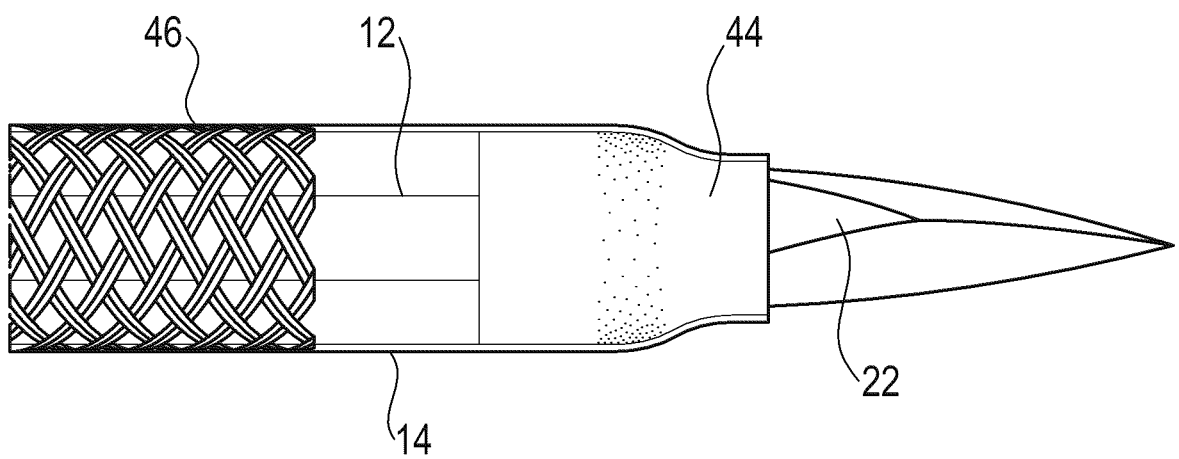
b)
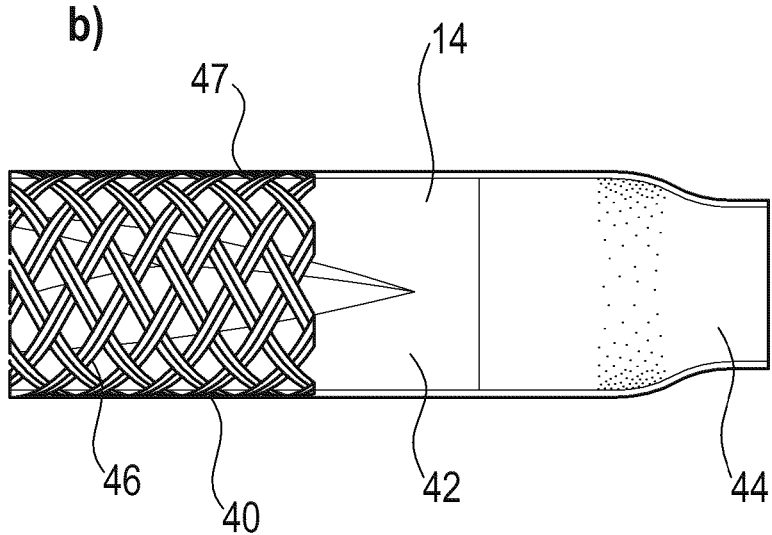

PUNCTURE DEVICE FOR CREATING A TIPS SHUNT AND CORRESPONDING METHODS

PRIORITY

This application is a U. S. national stage application of International Application No. PCT/EP2020/074432, filed Sep. 2, 2020, which is incorporated by reference in its entirety into this application.

TECHNICAL FIELD

The present invention relates to a puncture device for creating a TIPS shunt. The invention also relates to corresponding methods of treatment and assembly.

TECHNICAL BACKGROUND

In patients suffering from liver cirrhosis due to, for example, viral hepatitis or chronic alcohol abuse, a common problem is portal hypertension, i.e. a hypertension inside the liver. This hypertension in the hepatic portal system can lead to a significant number of medical conditions such as intestinal bleeding, oesophageal bleeding and the build-up of fluid within the abdomen (ascites).

In order to treat portal hypertension, a shunt is often artificially created within the liver that establishes a communication between the inflow portal vein and the outflow hepatic vein. Through this shunt, which is called a "transjugular intrahepatic portosystemic shunt" (also known as a "TIPS" or "TIPS shunt"), blood can bypass the diseased liver and flow directly from the inflow portal vein to the outflow hepatic vein without going through the liver. In that way, portal hypertension can be alleviated.

In order to create that shunt, a surgeon needs to artificially create a channel through the liver. In patients with late stage liver cirrhosis, the liver tissue is generally highly stiff. Accordingly, a trocar for cutting through the liver needs to exert a significant force and thus has to be somewhat flexurally rigid. On the other hand, it is generally the case that the devices for creating such shunts are catheters that are introduced through the patient's vasculature which requires a significant amount of bendability of the catheter. This requirement somewhat contradicts the need for it to be flexurally rigid.

A further challenge is that it is often not straightforward to correctly steer the catheter. The catheter is typically introduced into the hepatic vein, and the surgeon then aims to pierce the liver so as to establish a connection with the portal vein. A catheter that is typically used for that purpose has a puncture needle arranged within a sheath that tightly fits around the puncture needle. Such access sets are generally called "RUPS" ("Rösch-Uchida Portosystemic Shunt") TIPS access sets.

Once the surgeon believes that he has punctured the portal vein, the puncture needle is, in prior art devices, completely withdrawn whilst the sheath is left in place. Then, it is attempted to aspirate blood through the sheath. If blood can be aspirated, this is taken as a sign that the portal vein has been reached. If, however, no blood can be aspirated, this means that the portal vein has not been reached, and the surgeon needs to make another attempt at puncturing that vein.

The present inventors have realised that this is highly unpractical since one needs to withdraw the puncture needle in its entirety, which takes a lot of time. If the puncture attempt was unsuccessful, the puncture needle needs to be reinserted so as to be able to puncture again. Depending on how quickly the portal vein is punctured, the puncture needle has to be completely withdrawn and completely reinserted several times during a surgical procedure. This prolongs the time it takes for a TIPS shunt to be placed.

Additionally, the puncture needle has a pointed and rather sharp tip. A surgeon needs to be extremely careful in handling that tip since there is a risk of injury by puncturing himself with that tip. This becomes even more problematic in view of the fact that the patient's bodily fluids it was exposed to can be infectious. In particular in the case of patients suffering from viral hepatitis, this problem is a serious concern. Accordingly, given the care that needs to be exerted, a significant amount of time is required for the puncturing.

Another attempt at overcoming the previously mentioned issues is to use a hollow puncture needle to puncture the liver. With that technique, there is no need to remove the puncture needle since blood can be aspirated via the lumen of the needle itself. On the other hand, such puncture needles typically have a significant profile (about 1.3 mm) and can cause serious injury to the liver if several attempts to puncture the liver are required.

Therefore, a need exists for an improved puncture device for creating a TIPS shunt and for corresponding methods of creating a TIPS shunt and methods of assembling the puncture device.

SUMMARY OF THE INVENTION

The present invention has been conceived in view of the previously mentioned problems that were identified by the inventor and aims at solving or at least alleviating at least some of them.

The invention is defined by the product of claim 1 and by the methods of claims 9 and 12. Embodiments are defined in the dependent claims.

According to the invention, the puncture device for creating a TIPS shunt comprises a puncture needle that is, in embodiments, arranged as part of a catheter suitable for advancing through a patient's vasculature. This puncture needle is inserted into a tubular sheath forming part of the catheter and having open proximal and distal ends, with the sheath being arranged to surround the puncture needle. The puncture needle can be slid within the sheath so that it can be moved between a first position, in which the puncture needle has its distalmost tip, which is the sharp end, protrude beyond the distal end of the sheath, and a second position where the distalmost end of the puncture needle is retracted into the sheath. The sheath and the puncture needle are arranged so that in the second position, blood can be aspirated into the sheath from the open distal end of the sheath through a gap between the puncture needle and the sheath.

The arrangement of the puncture needle and the sheath can be introduced into a patient's vasculature and can be advanced to the liver through that vasculature. Accordingly, it has a cross-sectional diameter that is sufficiently small to allow for such an advancement. The device is arranged so that the puncture needle can be locked in the second and/or the first position. When the puncture needle is locked in the first position, the puncture needle does not move relative to the sheath during the puncturing, which makes the puncture device easy to use for a surgeon. When the puncture needle is locked in the second position, the surgeon does not need to worry about the puncture needle moving when aspirating blood.

By means of there being a gap between the puncture needle and the sheath when the puncture needle is in the second position, it is not necessary to completely withdraw the puncture needle from the puncture device in order to aspirate blood to check whether the portal vein has been reached. All that is required is to have a somewhat smaller withdrawal of the puncture needle which can otherwise stay within the sheath. In that way, the puncture device is less burdensome to use for a surgeon and also keeps the sharp puncture needle tip safely within the sheath and thus within the patient's body.

In embodiments, the device is arranged so that with the puncture needle in the first position, the puncture needle extends beyond the distal end of the lumen of the sheath and is arranged so as to prevent bodily fluids from entering the lumen through the distal end of the lumen. Put differently, the puncture needle seals the distal end of the lumen. This feature leads to an advantage in that it is avoided that bodily fluids enter into the gap between the sheath and the puncture needle during puncturing, which would otherwise make it difficult to subsequently determine whether the portal vein has been punctured (since bodily fluids would be present within that gap regardless of whether the hepatic vein has been punctured or not). This functionality is somewhat analogous to that of a needle valve.

In embodiments, the sheath has a distal portion that is tapering towards the distal end. In that way, also the sheath can force apart liver tissue when being advanced through that tissue so that the liver tissue is expanded not only by the puncture needle but also by the sheath. Further, the tapering shape reduces the forces that are applied to the sheath and that could otherwise compress it in the longitudinal direction. In further embodiments, the distal portion has the shape of a truncated cone. Such a truncated cone is rotationally symmetric and thus applies symmetric forces to the liver tissue during puncturing. This is advantageous since it avoids having localised higher stresses being applied to tissue.

In embodiments, the puncture needle has a pyramidal tip. Such a pyramidal tip, which could also be described as a square cut, leads to symmetric puncturing forces, which is particularly advantageous for puncturing whilst also being easy to manufacture.

In embodiments, the locking means is arranged so as to provide a locking force that is strong enough to hold the puncture needle in the first position when puncturing the parenchyma and, in embodiments, cirrhotic liver tissue. That is, when puncturing such liver tissue, it is not necessary for the surgeon to ensure that the puncture needle is held in place relative to the sheath, which improves the ease of use.

In embodiments, the puncture device comprises an adapter element that is provided at a proximal end of the sheath. This adapter element comprises a needle inlet through which the puncture needle is inserted. In embodiments, this needle inlet extends in a straight line from the sheath which makes it easier for a surgeon to use such a device. This applies in particular because a number of surgeons are used to using inline assemblies.

In embodiments, the adapter element further comprises a side port arranged so as to branch off from the adapter element at an angle relative to the needle inlet. In some embodiments, this angle could be 90°. This side port is arranged for injecting and/or aspirating fluid into and/or from the lumen of the sheath and can thus be used for checking whether the portal vein has been punctured. By having the side port arranged at an angle relative to the needle inlet, one avoids an interference between the tools such as a syringe used for aspirating fluid and the puncture needle. In some embodiments, the side port comprises a Luer connector. Such connectors are well known in the field of medicine and are hence user-friendly for a surgeon used to working with them. They also allow for easy attachment and detachment of syringes.

In embodiments, the needle inlet comprises a Luer connector. Such Luer connectors can be easily implemented and allow for easily locking the puncture needle in place, in particular when the puncture needle is in the first position.

In embodiments, the sheath comprises a proximal segment and a distal segment that are joined together. The distal segment is provided distally relative to the proximal segment. The proximal segment of the sheath comprises a stiffening structure that causes the proximal segment to have a higher flexural rigidity than the distal segment. Thanks to this higher flexural rigidity, the proximal segment can exert a larger force onto the liver parenchyma during puncturing, which makes puncturing easier. In embodiments, the stiffening structure comprises a braided and/or a coiled structure where the braids and/or coils can, in some embodiments, be made of wire or other reinforcing materials. Such reinforcing materials can be easily integrated into a catheter that comprises significant plastic components.

The invention also relates to a method of creating a TIPS shunt. The method comprises inserting a puncture device into a patient, the puncture device having the features as defined previously. Subsequently to that insertion, the puncture needle of the puncture device is transitioned from a first position, in which the distal tip of the puncture needle is within the sheath, to a second position, in which the distal tip protrudes beyond a distal end of the sheath. Afterwards, the surgeon locks the puncture needle in the second position and then punctures the portal vein of the patient's liver. This leads to advantages corresponding to those discussed earlier for corresponding features.

In embodiments, there is the further step of transitioning the puncture needle from the second position to the first position; and of aspirating blood through the sheath around an annular gap between the outer surface of the puncture needle and an inner surface of the sheath. Accordingly, the surgeon can check whether he or she has punctured the portal vein.

In that context, embodiments further comprise locking the puncture needle in the first position before aspirating. This prevents the puncture needle from shifting in position during aspiration.

The invention also relates to a method of assembling a puncture device according as defined previously. The method comprises the steps of providing the puncture needle, providing the sheath, providing the locking means, and of arranging the puncture needle inside the sheath so that the locking means releasably locks the puncture needle in the first position or the second position relative to the sheath. These steps, which do not necessarily have to be carried out in the stated order, lead to a puncture device that has the claimed advantages when it comes to creating a TIPS shunt.

BRIEF DESCRIPTION OF THE DRAWINGS

FIG. 3 is a close-up view of the tip of the puncture device for creating a TIPS shunt according to an embodiment of the invention.

DETAILED DESCRIPTION OF THE DRAWINGS

Figure 1:
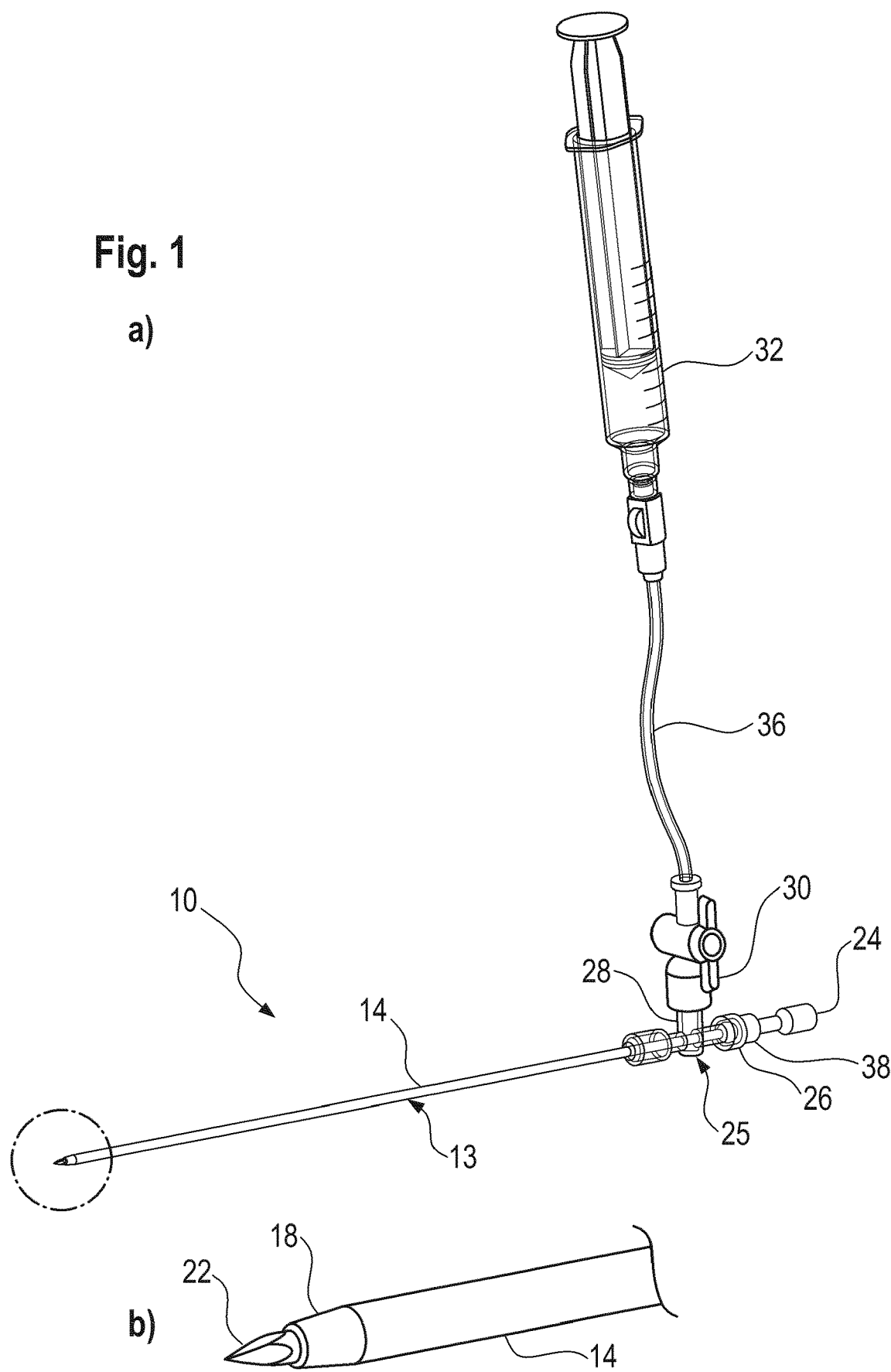
FIG. 1 shows a puncture device for creating a TIPS shunt according to an embodiment of the invention with the puncture needle in the first position.

FIG. 1 shows a puncture device 10 that can be used for creating a TIPS shunt. FIG. 1a) shows the whole puncture device 10 whilst FIG. 1b) shows a close-up of the tip.

The puncture device 10 comprises a sheath 14. Inside sheath 14 is arranged a puncture needle 12 that has a pyramidal tip 22.

At the distal end of the sheath 14 is provided a distal portion 18 that has the shape of a truncated cone. The sheath 14 and the puncture needle 12 form together catheter 13.

Turning now attention to the proximal end of the puncture device 10, there is provided, at the proximal end of the sheath 14, an adapter element 25. This adapter element 25 comprises a needle inlet 26 through which the puncture needle 12 can be introduced into and withdrawn from the sheath 14 and a side port 28 arranged at roughly right angles to the needle inlet 26. Through the side port 28, a liquid can be aspirated via the sheath 14. There is furthermore provided a locking means 38 that is arranged on the puncture needle 12 at a proximal end thereof. A Luer connector 24 is provided proximally to that end that is also part of the puncture needle 12. The locking means 38 can be locked inside the needle inlet 26. In that configuration, as shown in FIG. 1a) and, in an enlarged form, FIG. 1b), the tip 22 of the puncture needle 12 protrudes beyond the distal portion 18 of the sheath 14 and is held, by locking means 38, in that position so that when puncturing liver tissue, the puncture needle 12 will be retained in the position relative to sheath 14 that is shown in FIGS. 1a) and 1b).

Locking means 38 can, for example, comprise one or more threads that allow for a releasable connection between the locking means 38 and the inside of the inlet port 26 of the adapter element 25. However, other ways of designing such a locking means 38 are also possible (such as, for example, the locking means 38 having the form of a Luer connector that engages with corresponding threads inside the inlet port 26, the locking means 38 having a protrusion that engages with a notch or a latch that is provided inside the inlet port 26, . . . ).

The skilled person can conceive of further ways of implementing the locking means.

The side port 28 is connected to a side port connector 30 that is, in turn connected to a flexible tube 36. The flexible tube 36 is connected to a syringe 32. Through that syringe 32 and the tube 36, liquid can be aspirated via the sheath 14.

In the configuration that it is shown in FIGS. 1a) and b), the tip 22 of the puncture needle 12 closes the distal end 11 of the lumen of the sheath 14 in a fluid tight manner. In that way, in the configuration shown in FIG. 1, liquid cannot be aspirated since the opening is sealed.

Figure 2:
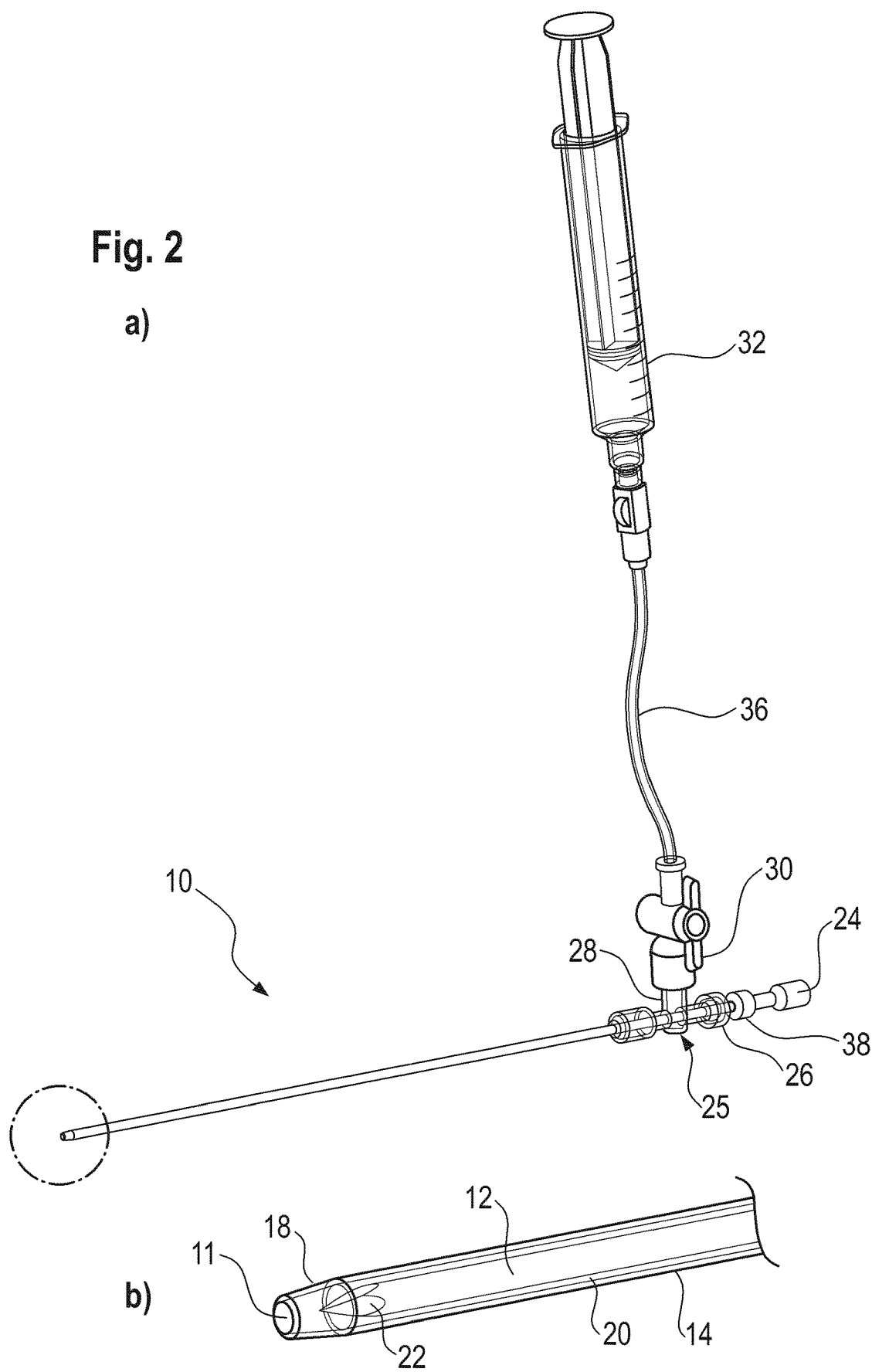
FIG. 2 shows the puncture device of FIG. 1 when the puncture needle is in the second position.

FIG. 2 shows in FIG. 2a) and FIG. 2b) a configuration of the device shown in FIG. 1 that is suitable for aspirating bodily fluids via the sheath 14.

As can be seen more clearly from FIG. 2b), in this configuration, puncture needle 12 is withdrawn relative to sheath 14 so that puncture needle 12 no longer distally extends relative to the sheath 14. Accordingly, the distal end 11 of the lumen of the sheath 14 is no longer occluded by the puncture needle 12. Thus, in that configuration, a fluid such as blood can be aspirated via a gap 20 between the puncture needle 12 to sheath 14 so that a surgeon can determine whether the portal vein has been punctured. This configuration corresponds to the puncture needle 12 being in the second position relative to the sheath 14.

In the configuration shown in FIG. 2, the locking means 38 is withdrawn relative to the inlet port 26. However, also in that configuration, the puncture needle 12 is locked in that position, for example by means of a protrusion provided on the puncture needle 12 that engages with a corresponding recess in the adapter member 25. This engagement holds the puncture needle 12 in place relative to sheath 14.

FIG. 3a) and FIG. 3b) show the first and the second position, respectively, of the puncture needle 12 relative to the sheath 14. As can be seen from FIG. 3a), the tip 22 of the puncture needle 12 protrudes beyond the distal end of the sheath 14. It passes through a ring-shaped lip 44 that is be made of a flexible and compliant material so as to provide a tight seal around the puncture needle 12. In FIG. 3b), the puncture needle 12 has been withdrawn by a few millimetres so that the tip 22 no longer extends distally beyond the end of the sheath 14. Accordingly, in that configuration, a gap opens between the puncture needle 12 and the sheath which allows for aspirating blood through that gap by means of withdrawing the piston of a syringe (not shown) that is connected to the sheath 14. If the surgeon has successfully punctured the portal vein, blood will be aspirated, which can be detected (e.g. visually) by the surgeon. If that is the case, the puncture needle 12 can be withdrawn and be replaced by a guidewire (not shown) so as to place a TIPS stent graft (not shown). Accordingly, the method of operation is quite similar to the way a RUPS access set is used, which makes it easy for the surgeon to transition to this new system.

In the configuration that is shown in FIGS. 3a) and 3b), the sheath 14 is part of a 5 French catheter, and the puncture needle 12 has a diameter of 0.95 mm, which is smaller than the inner diameter of the sheath 14. The annular gap between the needle 12 and the sheath 14 was about 0.08 mm, with a preferred range of between 0.06 and 0.1 mm.

The sheath 14 also comprises a proximal segment 40 that is provided proximally relative to distal segment 42. The proximal segment 40 comprises a stiffening structure in the form of metal threads that are arranged in a braided manner so as to stiffen the plastic material of the sheath 14. This leads to a higher flexural rigidity of the proximal segment 40 compared with the distal segment 42. The metal wires can be arranged so as to leave some gaps 47 between them so that even though the flexural rigidity is increased, there is still some scope for bending the sheath 14. It is also conceivable to use coiled wires for the same purpose.

Figure 4:
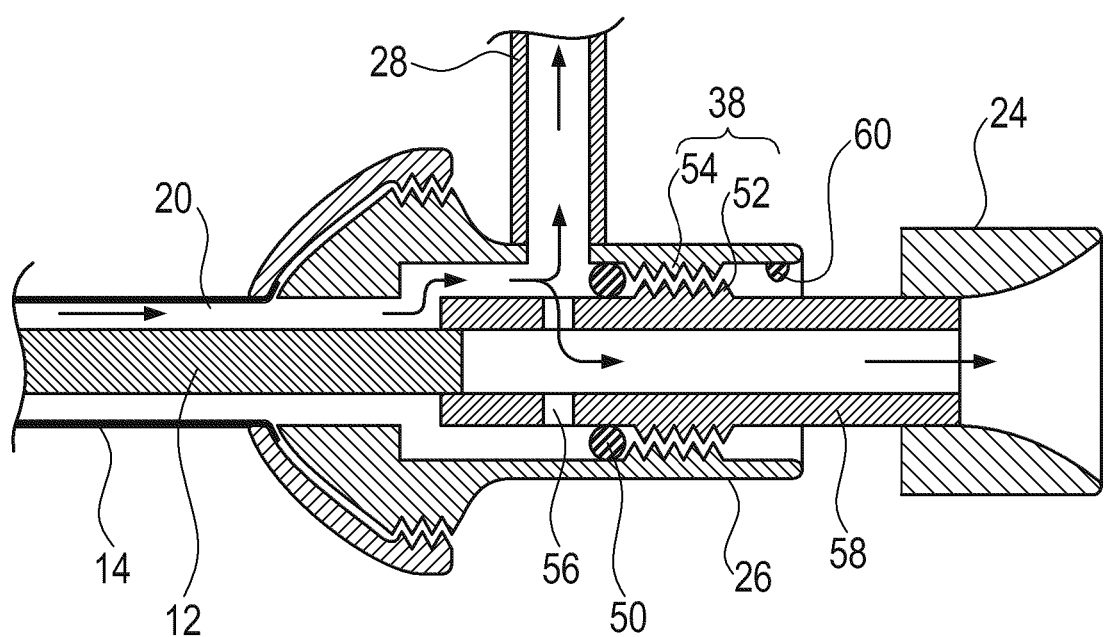
FIG. 4 is a cross-sectional view of the proximal end of the puncture device according to an embodiment of the invention.

In FIG. 4, the configuration of the proximal end of the puncture device 10 is shown. The needle 12 is arranged inside the sheathlike needle inlet 26. The needle 12 itself comprises a hollow cylindrical portion 58 that is connected to the female Luer connector 24. Provided so as to penetrate the walls of the hollow cylindrical portion 58 are openings 26 that connect between the gap 20 and the lumen of the hollow cylindrical portion. The side port 28 is also fluidically connected to the gap 20. Accordingly, a fluid flow (indicated by arrows) through the gap 20 can leave through the side port 28 and also—via openings 56—through the female Luer connector 24.

The needle 14 is held inside the needle inlet 26 by means of threads 52, 54 that are provided on the needle 14 and the needle inlet 26, respectively. There is further provided a sealing element 50 (e.g. an O-ring) that seals between the needle 14 and the needle inlet 26. The configuration shown in FIG. 4 corresponds to the configuration shown in FIGS. 1a), b) where the needle 12 is fully extended. The needle 14 is held in that position by the engagement between the threads 52, 54. Thus, the threads 52, 54 function as the locking means 38.

If the user now twists the needle 14 relative to the needle inlet 26, the needle 14 is moved proximally relative to the needle inlet 26, so that the puncture device 10 transitions from the configuration shown in FIG. 1 to the configuration shown in FIG. 2. In order to avoid withdrawing the needle 14 too far outside of the needle inlet 26, a protrusion 60 is provided on the needle inlet 26 that abuts against the threads 52 of the needle 14 when the needle 14 is rotated relative to the needle inlet 26. This abutment prevents an inadvertent complete withdrawal of the needle 14. If it is, however, desired to completely withdraw the needle 14, the engagement between the protrusion 60 and the threads 52 can be overcome by applying a substantially large pulling force. Alternative ways of achieving the same or similar functionalities would be to provide a lug that could be brought out of engagement with the needle 14. The skilled person will be able to envisage other ways in which this feature can be implemented.

It is to be noted that the configuration shown in FIG. 4, where a fluid can be aspirated either via the side port 28 or the Luer connector 24 allows for a greater amount of flexibility. Some surgeons prefer to use an inline puncture device 10. If that is desired, the side port 28 can be closed. Other surgeons prefer to use the side port 28, in which case the Luer connector 24 can be closed.

The inventors used stainless steel wires (ANSI 304 SS) for the braiding with cross-sectional dimensions of about 0.025×0.075 mm. However, other wires can also be used, and it is also conceivable that non-metallic but sufficiently stiff plastic threads can also be used for the braiding.

A good braiding angle was found to be 45°-60° relative to the longitudinal axis, which led to a good compromise between torsional rigidity, flexibility and rigidity when it comes to piercing tissue. This corresponds to a braiding density of between 54 ppi bis 93 ppi (picks per inch), assuming that there are 16 stands (8 strands braided in a clockwise fashion, 8 strands braided in a counterclockwise fashion).

The invention claimed is:

1. A puncture device for creating a TIPS shunt, comprising:
   a solid puncture needle,
   a sheath being arranged to surround the puncture needle, the puncture needle being slidably arranged inside the sheath so that the puncture needle can be moved between a first position in which the puncture needle protrudes beyond a distal end of the sheath and a second position where a tip of the puncture needle is retracted into the sheath, the sheath and the puncture needle being arranged so that in the second position, blood can be aspirated into the sheath through a gap between the puncture needle and the sheath,
   a locking means being arranged for releasably locking the puncture needle in the first position and the second position, and
   a hollow cylindrical portion connected to a proximal end of the puncture needle, the hollow cylindrical portion providing a fluid flow path for aspirated blood.

2. The puncture device according to claim 1, the puncture device being arranged so that in the first position, the puncture needle extends beyond a distal end of a lumen of the sheath so as to prevent a liquid from entering the lumen through the distal end of the lumen.

3. The puncture device according to claim 1, the sheath having a distal portion that is tapering towards the distal end, the distal portion preferably having a shape of a truncated cone.

4. The puncture device according to claim 1, the puncture needle having a pyramidal tip.

5. The puncture device according to claim 1, the locking means being arranged so as to provide a locking force that is strong enough to hold the puncture needle in the first position when puncturing diseased liver parenchyma.

6. The puncture device according to claim 1, the puncture device further comprising an adapter element, the adapter element comprising a needle inlet through which the puncture needle is inserted, the adapter element preferably further comprising a side port arranged so as to branch off from the adapter element at an angle relative to the needle inlet, the side port being arranged for injecting and/or aspirating fluid into and/or from a lumen of the sheath, the side port preferably comprising a luer connector.

7. The puncture device according to claim 6, the needle inlet comprising a luer connector.

8. The puncture device according to claim 1, the sheath comprising a proximal segment and a distal segment that is joined to the proximal segment, the proximal segment comprising a stiffening structure that causes the proximal segment to have a higher flexural rigidity than the distal segment, the stiffening structure preferably comprising a braided and/or a coiled structure.

9. The puncture device according to claim 1, the hollow cylindrical portion being in fluid communication with a luer connector.

10. The puncture device according to claim 9, the luer connector positioned proximal of the locking means.

11. The puncture device according to claim 9, the hollow cylindrical portion including one or more side openings fluidly connecting the gap between the puncture needle and the sheath with the luer connector.

12. A method of assembling a puncture device according to claim 1, the method comprising:
   providing the puncture needle,
   providing the sheath,
   providing the locking means, and
   arranging the puncture needle inside the sheath so that the locking means releasably locks the puncture needle in the first position or the second position relative to the sheath.

* * * * *